United States Patent
Tinnemans et al.

(10) Patent No.: US 10,267,744 B2
(45) Date of Patent: Apr. 23, 2019

(54) ILLUMINATION SOURCE FOR AN INSPECTION APPARATUS, INSPECTION APPARATUS AND INSPECTION METHOD

(71) Applicant: ASML Netherlands B.V., Veldhoven (NL)

(72) Inventors: Patricius Aloysius Jacobus Tinnemans, Hapert (NL); Nan Lin, Eindhoven (NL); Sander Bas Roobol, Veldhoven (NL); Simon Gijsbert Josephus Mathijssen, Rosmalen (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/641,579

(22) Filed: Jul. 5, 2017

(65) Prior Publication Data

US 2018/0011029 A1 Jan. 11, 2018

(30) Foreign Application Priority Data

Jul. 5, 2016 (EP) .................................. 16178048
Jul. 28, 2016 (EP) .................................. 16181778

(51) Int. Cl.
*G02F 1/35* (2006.01)
*G01N 21/47* (2006.01)
(Continued)

(52) U.S. Cl.
CPC ..... *G01N 21/8806* (2013.01); *G01N 21/4788* (2013.01); *G01N 21/956* (2013.01);
(Continued)

(58) Field of Classification Search
CPC ..................... G01B 9/02003; G01B 9/02007
See application file for complete search history.

(56) References Cited

U.S. PATENT DOCUMENTS 4,148,701 A * 4/1979 Leach .................... B01J 19/121
204/157.5
4,193,879 A * 3/1980 Leach .................... B01J 19/121
359/345

(Continued)

FOREIGN PATENT DOCUMENTS

CN         104330398        2/2015
EP       1 988 425 B1       7/2014
WO    WO 2013/171464 A1    11/2013

OTHER PUBLICATIONS

International Search Report and Written Opinion directed to International Patent Application No. PCT/EP2017/064362, dated Sep. 4, 2017; 18 pages.

(Continued)

*Primary Examiner* — Shawn Decenzo
(74) *Attorney, Agent, or Firm* — Sterne, Kessler, Goldstein & Fox P.L.L.C.

(57) ABSTRACT

Disclosed is an illumination source for generating measurement radiation for an inspection apparatus. The source generates at least first measurement radiation and second measurement radiation such that the first measurement radiation and the second measurement radiation interfere to form combined measurement radiation modulated with a beat component. The illumination source may be a HHG source. Also disclosed is an inspection apparatus comprising such a source and an associated inspection method.

19 Claims, 4 Drawing Sheets

(51) Int. Cl.
   *G01N 21/88*  (2006.01)
   *G01N 21/956* (2006.01)
   *G03F 7/20*   (2006.01)

(52) U.S. Cl.
   CPC .......... *G02F 1/353* (2013.01); *G03F 7/70008* (2013.01); *G03F 7/70616* (2013.01); *G01N 2021/95676* (2013.01); *G01N 2201/0697* (2013.01)

(56) References Cited

U.S. PATENT DOCUMENTS

| | | | | |
|---|---|---|---|---|
| 4,710,026 | A * | 12/1987 | Magome | G03F 7/70633 356/400 |
| 5,673,096 | A * | 9/1997 | Dorsel | A61B 3/1005 351/205 |
| 5,682,239 | A * | 10/1997 | Matsumoto | G03F 7/70633 250/548 |
| 6,335,625 | B1 * | 1/2002 | Bryant | G01N 23/00 324/316 |
| 6,831,935 | B2 * | 12/2004 | Ye | H01S 3/1109 372/18 |
| 8,466,247 | B2 | 6/2013 | Käsmayr et al. | |
| 9,203,209 | B2 | 12/2015 | Ramachandran | |
| 2006/0066855 | A1 | 3/2006 | Boef et al. | |
| 2011/0102753 | A1 | 5/2011 | Van De Kerkhof et al. | |
| 2011/0140009 | A1 * | 6/2011 | Kaertner | H05G 2/00 250/504 R |
| 2012/0044470 | A1 | 2/2012 | Smilde et al. | |
| 2013/0194582 | A1 * | 8/2013 | Tokimitsu | G01B 11/14 356/498 |
| 2013/0209926 | A1 * | 8/2013 | Oshemkov | C03C 23/0025 430/5 |
| 2014/0340666 | A1 * | 11/2014 | Butler | G03F 7/704 355/72 |
| 2015/0086148 | A1 * | 3/2015 | Liu | G02F 1/3544 385/1 |
| 2017/0184511 | A1 * | 6/2017 | Den Boef | G03F 9/7065 |
| 2018/0073992 | A1 * | 3/2018 | Van Voorst | G01N 21/8806 |

OTHER PUBLICATIONS

Kanai et al., "Heterodyne Interferometry Using High Harmonic Generation in Mixed Gases," OSA, 2008; 2 pages.

Shelton et at., "Synchronization and phase lock of two mode-locked femtosecond lasers," SPIE, vol. 4269, 2001; pp. 105-111.

Zerne et al., "Phase-locked high-order harmonic sources," Physical Review Letters, The American Physical Society, vol. 79, No. 6, Aug. 11, 1997; pp. 1006-1009.

* cited by examiner

ILLUMINATION SOURCE FOR AN INSPECTION APPARATUS, INSPECTION APPARATUS AND INSPECTION METHOD

FIELD

The present invention relates to a lithographic apparatus and a method for performing a measurement. In particular, it relates to an inspection apparatus comprised in a lithographic apparatus, and in particular its illumination source, as well as a method for performing a measurement therewith.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Multiple layers, each having a particular pattern and material composition, are applied to define functional devices and interconnections of the finished product.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field.

Examples of known scatterometers often rely on provision of dedicated metrology targets. For example, a method may require a target in the form of a simple grating that is large enough that a measurement beam generates a spot that is smaller than the grating (i.e., the grating is underfilled). In so-called reconstruction methods, properties of the grating can be calculated by simulating interaction of scattered radiation with a mathematical model of the target structure. Parameters of the model are adjusted until the simulated interaction produces a diffraction pattern similar to that observed from the real target.

In addition to measurement of feature shapes by reconstruction, diffraction-based overlay can be measured using such apparatus, as described in published patent application US2006066855A1. Diffraction-based overlay metrology using dark-field imaging of the diffraction orders enables overlay measurements on smaller targets. These targets can be smaller than the illumination spot and may be surrounded by product structures on a wafer. Examples of dark field imaging metrology can be found in numerous published patent applications, such as for example US2011102753A1 and US20120044470A. Multiple gratings can be measured in one image, using a composite grating target. The known scatterometers tend to use light in the visible or near-IR wave range, which requires the pitch of the grating to be much coarser than the actual product structures whose properties are actually of interest. Such product features may be defined using deep ultraviolet (DUV) or extreme ultraviolet (EUV) radiation having far shorter wavelengths. Unfortunately, such wavelengths are not normally available or usable for metrology.

On the other hand, the dimensions of modern product structures are so small that they cannot be imaged by optical metrology techniques. Small features include for example those formed by multiple patterning processes, and/or pitch-multiplication. Hence, targets used for high-volume metrology often use features that are much larger than the products whose overlay errors or critical dimensions are the property of interest. The measurement results are only indirectly related to the dimensions of the real product structures, and may be inaccurate because the metrology target does not suffer the same distortions under optical projection in the lithographic apparatus, and/or different processing in other steps of the manufacturing process. While scanning electron microscopy (SEM) is able to resolve these modern product structures directly, SEM is much more time consuming than optical measurements. Moreover, electrons are not able to penetrate through thick process layers, which makes them less suitable for metrology applications. Other techniques, such as measuring electrical properties using contact pads is also known, but it provides only indirect evidence of the true product structure.

By decreasing the wavelength of the radiation used during metrology (i.e. moving towards the "soft X-ray" wavelength spectrum), it is possible to resolve smaller structures, to increase sensitivity to structural variations of the structures and/or penetrate further into the product structures. However, this likely requires a corresponding improvement in the spectral resolution of the metrology system. Additionally, the complexity of product structures is increasing, with product structures comprising increasing numbers of layers and a corresponding increase in thickness. This, in turn, increases the spectral resolution required to perform metrology measurements.

SUMMARY

The present invention aims to provide an alternative inspection apparatus and method for performing measurements of the type described above.

According to a first aspect of the present invention, there is provided an illumination source for generating measurement radiation for an inspection apparatus operable to generate at least first measurement radiation and second measurement radiation such that said first measurement radiation and said second measurement radiation interfere to form combined measurement radiation modulated with a beat component.

According to a second aspect of the present invention, there is provided an illumination source for generating high harmonic radiation, operable to generate at least first high harmonic radiation and second high harmonic radiation such that said first high harmonic radiation and said second high harmonic radiation interfere to form combined high harmonic radiation modulated with a beat component.

According to a third aspect of the present invention, there is provided a method of measuring a target structure on a substrate comprising: generating at least first measurement radiation and a second measurement radiation such that said first measurement radiation and said second measurement radiation interfere to form combined measurement radiation modulated with a beat component; illuminating the target structure with the measurement radiation resulting in scattered radiation modulated with the beat component; detecting the scattered radiation; and processing the detected scattered radiation, said processing comprising using said beat component to spectrally resolve said scattered radiation.

According to a third aspect of the present invention, there is provided an inspection apparatus, comprising: an illumination source of the first or second aspect, operable to provide measurement radiation modulated with a beat component; an illumination system operable to illuminate a target structure with the measurement radiation resulting in scattered radiation modulated with the beat component; a detector operable to detect the scattered radiation; and a processor operable to use said beat component to spectrally resolve said scattered radiation.

The invention yet further provides a computer program product containing one or more sequences of machine-readable instructions for implementing controlling steps in a method according to the invention as set forth above.

Further aspects, features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Before describing embodiments of the invention in detail, it is instructive to present an example environment in which embodiments of the present invention may be implemented.

Figure 1:
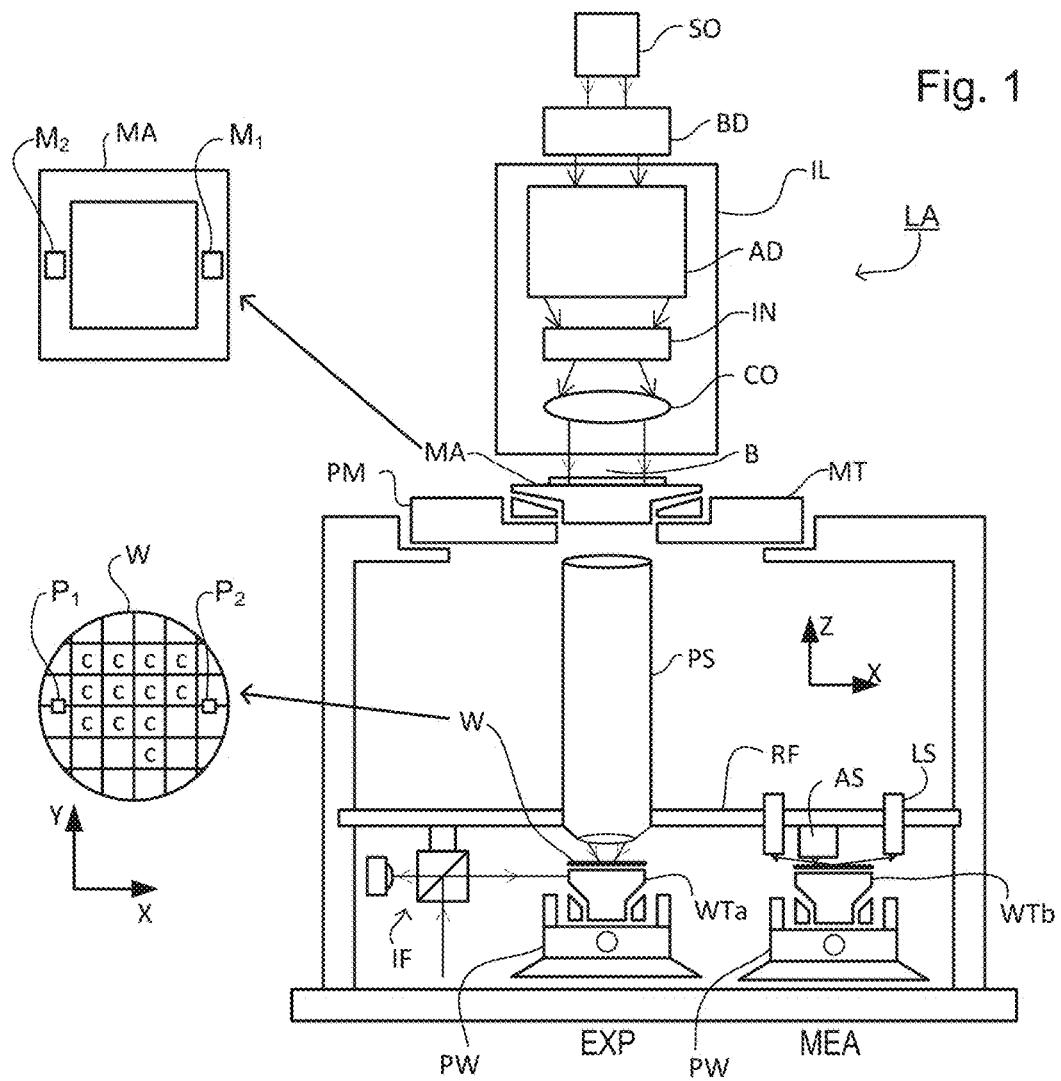
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV or EUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support MT may be a frame or a table, for example, which may be fixed or movable as required. The patterning device support may ensure that the patterning device is at a desired position, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable LCD panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

In operation, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment mark may also be included within dies, in amongst the device features, in which case it is desirable that the markers be as small as possible and not require any different imaging or process conditions than adjacent features. The alignment system, which detects the alignment markers is described further below.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The speed and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment markers on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements are known and usable instead of the dual-stage arrangement shown. For example, other lithographic apparatuses are known in which a substrate table and a measurement table are provided. These are docked together when performing preparatory measurements, and then undocked while the substrate table undergoes exposure.

Figure 2:
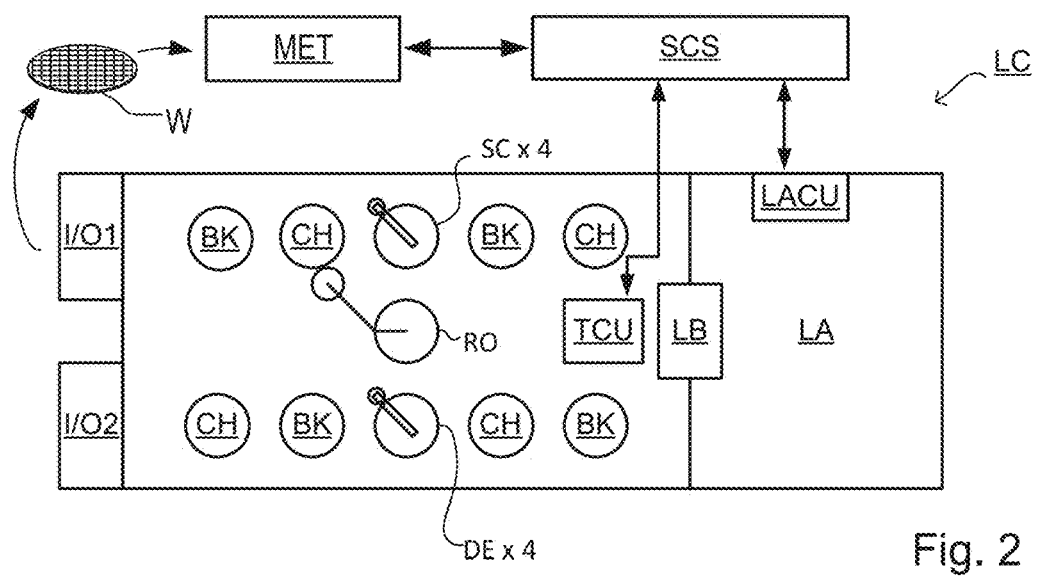
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

The substrates processed by the track are then transferred to other processing tools for etching and other chemical or physical treatments within the device manufacturing process. In some instances, metrology may be performed on substrates after such etching or chemical/physical treatment steps.

The lithographic apparatus control unit LACU controls all the movements and measurements of the various actuators and sensors described. LACU also includes signal processing and data processing capacity to implement desired calculations relevant to the operation of the apparatus. In the terminology of the introduction and claims, the combination of these processing and control functions referred to simply as the "controller". In practice, control unit LACU will be realized as a system of many sub-units, each handling the real-time data acquisition, processing and control of a subsystem or component within the apparatus. For example, one processing subsystem may be dedicated to servo control of the substrate positioner PW. Separate units may even handle coarse and fine actuators, or different axes. Another unit might be dedicated to the readout of the position sensor IF. Overall control of the apparatus may be controlled by a central processing unit, communicating with these subsystems processing units, with operators and with other apparatuses involved in the lithographic manufacturing process.

Figure 3A:
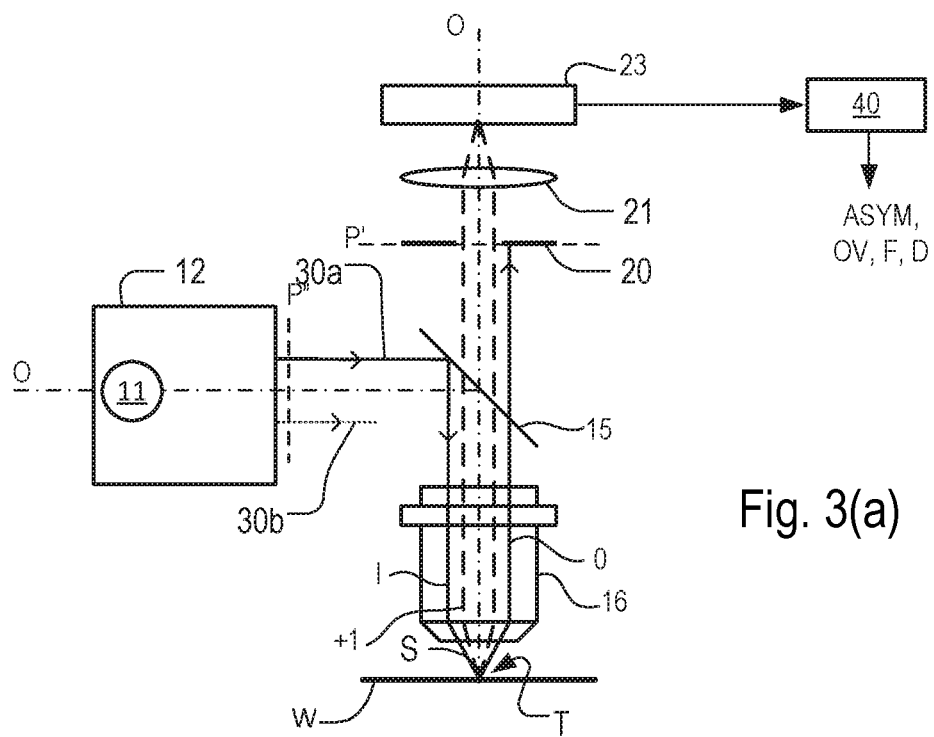
FIGS. 3(a) and 3(b) illustrate schematically an inspection apparatus adapted to perform a known dark-field imaging inspection methods.

FIG. 3(a) shows schematically the key elements of an inspection apparatus implementing so-called dark field imaging metrology. The apparatus may be a stand-alone device or incorporated in either the lithographic apparatus LA, e.g., at the measurement station, or the lithographic cell LC. An optical axis, which has several branches throughout the apparatus, is represented by a dotted line O. A target grating structure T and diffracted rays are illustrated in more detail in FIG. 3(b).

As described in the prior applications cited in the introduction, the dark-field-imaging apparatus of FIG. 3(a) may be part of a multi-purpose angle-resolved scatterometer that may be used instead of or in addition to a spectroscopic scatterometer. In this type of inspection apparatus, radiation emitted by a radiation source 11 is conditioned by an illumination system 12. For example, illumination system 12 may include a collimating lens system, a color filter, a polarizer and an aperture device. The conditioned radiation follows an illumination path, in which it is reflected by partially reflecting surface 15 and focused into a spot S on substrate W via a microscope objective lens 16. A metrology target T may be formed on substrate W. Lens 16, has a high numerical aperture (NA), preferably at least 0.9 and more preferably at least 0.95. Immersion fluid can be used to obtain with numerical apertures over 1 if desired. The multi-purpose scatterometer may have two or more measurement branches. Additionally, further optical systems and branches will be included in a practical apparatus, for example to collect reference radiation for intensity normalization, for coarse imaging of capture targets, for focusing and so forth. Details of these can be found in the prior publications mentioned above. For the purposes of the present disclosure, only the measurement branch of interest for the dark-filed imaging metrology is illustrated and described in detail.

In the collection path for dark-field imaging, imaging optical system 21 forms an image of the target on the substrate W on sensor 23 (e.g. a CCD or CMOS sensor). An aperture stop 20 is provided in a plane P' in the collection path. Plane P' is a plane conjugate to a pupil plane P (not shown) of objective lens 16. Aperture stop 20 may also be called a pupil stop. Aperture stop 20 can take different forms, just as the illumination aperture can take different forms. The aperture stop 20, in combination with the effective aperture of lens 16, determines what portion of the scattered radiation is used to produce the image on sensor 23. Typically, aperture stop 20 functions to block the zeroth order diffracted beam so that the image of the target formed on sensor 23 is formed only from the first order beam(s). In an example where both first order beams are combined to form an image, this would be the so-called dark field image, equivalent to dark-field microscopy. In the present application, however, only one of the first orders is imaged at a time, as explained below. The images captured by sensor 23 are output to image processor and controller 40, the function of which will depend on the particular type of measurements being performed. For the present purpose, measurements of asymmetry of the target structure are performed. Asymmetry measurements can be combined with knowledge of the target structures to obtain measurements of performance parameters of lithographic process used to form them. Performance parameters that can be measured in this way include for example overlay, focus and dose.

Where a metrology target T is provided on substrate W, this may be a 1-D grating, which is printed such that after development, the bars are formed of solid resist lines. The target may be a 2-D grating, which is printed such that after development, the grating is formed of solid resist pillars or vias in the resist. The bars, pillars or vias may alternatively be etched into the substrate. Each of these gratings is an example of a target structure whose properties may be investigated using the inspection apparatus.

The various components of illumination system 12 can be adjustable to implement different metrology 'recipes' within the same apparatus. In addition to selecting wavelength (color) and polarization as characteristics of the particular, illumination system 12 can be adjusted to implement different illumination profiles. Because plane P'' is conjugate with pupil plane P of objective lens 16 and the plane of the detector 19, an illumination profile in plane P'' defines the angular distribution of light incident on substrate W in spot S. To implement different illumination profiles, an aperture device can be provided in the illumination path. The aperture device may comprise different apertures mounted on a movable slide or wheel. It may alternatively comprise a programmable spatial light modulator. As a further alternative, optical fibers may be disposed at different location in the plane P'' and used selectively to deliver light or not deliver light at their respective locations. These variants are all discussed and exemplified in the documents cited above.

In a first example illumination mode, rays 30a are provided so that the angle of incidence is as shown at 'I' and the path of the zero order ray reflected by target T is labeled '0' (not to be confused with optical axis 'O'). In a second illumination mode, rays 30b can be provided, in which case the angles of incidence and reflection will be swapped. Both of these illumination modes will be recognized as off-axis illumination modes. Many different illumination modes can be implemented for different purposes.

Figure 3B:
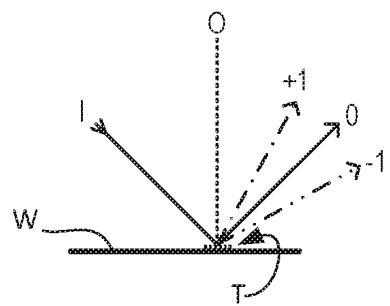

As shown in more detail in FIG. 3(b), target grating T as an example of a target structure is placed with substrate W normal to the optical axis O of objective lens 16. In the case of an off-axis illumination profile, a ray of illumination I impinging on grating T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the beam of illuminating rays 30a has a finite width (necessary to admit a useful quantity of light), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown.

Referring also to FIG. 3(a), under the first illumination mode with rays 30a, +1 order diffracted rays from the target grating will enter the objective lens 16 and contribute to the image recorded at sensor 23. When the second illumination mode is used, rays 30b are incident at an angle opposite to rays 30b, and so the −1 order diffracted rays enter the objective and contribute to the image. Aperture stop 20 blocks the zeroth order radiation when using off-axis illumination. As described in the prior publications, illumination modes can be defined with off-axis illumination in X and Y directions.

By comparing images of the target grating under these different illumination modes, asymmetry measurements can be obtained. Alternatively, asymmetry measurements could be obtained by keeping the same illumination mode, but rotating the target. While off-axis illumination is shown, on-axis illumination of the targets may instead be used and a modified, off-axis aperture 20 could be used to pass substantially only one first order of diffracted light to the sensor. In a further example, prisms are used in place of aperture stop 20 which have the effect of diverting the +1 and −1 orders to different locations on sensor 23 so that they can be detected and compared without the need for two sequential image capture steps. This technique, is disclosed in the above-mentioned published patent application US2011102753A1, the contents of which are hereby incorporated by reference. 2nd, 3rd and higher order beams (not shown in FIG. 3) can be used in measurements, instead of or in addition to the first order beams. As a further variation, the off-axis illumination mode can be kept constant, while the target itself is rotated 180 degrees beneath objective lens 16 to capture images using the opposite diffraction orders.

The above techniques are typically performed using radiation with a visible wavelength. As such, the scatterometry targets have a pitch that is larger than that of the product structures on the substrate. As an example, a scatterometry target may have a target grating pitch measured in microns (μm), whereas product structures on the same substrate may have a pitch measured in nanometers (nm).

This difference in pitch induces an offset between the measured overlay and the actual overlay on the product structures. The offset is at least partly due to optical projection distortions in the lithographic apparatus and/or different processing in other steps of the manufacturing process. Presently, the offset comprises a significant contribution to the overall measured overlay. Reducing or eliminating it will therefore improve overall overlay performance.

Metrology tools may be developed which use sources that emit radiation in "soft X-ray" or EUV range, for example having wavelengths between 2 nm and 50 nm. Examples of such sources include Discharge Produced Plasma sources, Laser Produced Plasma Sources or High-order Harmonic Generation (HHG) sources. HHG sources are known to be able to provide large flux of collimated photons (high luminance) in the emitted light.

HHG sources used in metrology applications are illustrated and further described in the European patent applications EP152020301, EP16168237, EP16167512, which are hereby incorporated in their entirety by reference. In metrology applications, such HHG sources may be used (for example) in normal incidence, very close to normal incidence (e.g., within 10 degrees from normal), at a grazing incidence (e.g., within 20 degrees from surface), at an arbitrary angle or at multiple angles (to obtain more measurement information in a single capture).

In order to maximize the accuracy of a diffraction-based measurement, e.g. to determine overlay error or critical dimension, it is necessary to optimize the properties of the radiation that arrives at the detector. The property of the scattered radiation is dependent the properties of the radiation used and the properties of the structure under measurement. In order to increase the number of photons, for example, a large bandwidth source may be used, e.g., emitting radiation of wavelengths spanning 8 nm-20 nm or more. Such a large bandwidth source also provides greater information for a single measurement, as (for example) different structures, structure densities and/or materials may demonstrate different measurement sensitivity with different wavelengths. The ability to correlate measurements using measurement radiation of different wavelengths makes the measurement more robust. However, a large bandwidth source may result in the problem of overlapping diffraction orders in a target measurement, and also requires the metrology tool to have good spectral resolution, particularly when the wavelengths are comparable sized or smaller than the thickness of the structures being measured.

One parameter that may be used to describe the quality of the scattered radiation is the so-called "stack sensitivity". This parameter describes the strength of a measured signal (e.g., an asymmetry measurement). It can be shown that such "stack sensitivity" varies periodically in dependence on the wavelength of the radiation and the thickness of the target structure. The period of the variation $\Delta\lambda_s$, which determines the resolution for a stack thickness T, can be described as:

$$\Delta\lambda_s = \frac{\lambda^2}{2T} \quad (1)$$

where $\lambda$ is the wavelength of the radiation, and T is the optical thickness of the structure being measured. An exemplary optical thickness of a product structure may be 400 nm, and an exemplary radiation wavelength may be $\lambda$=13 nm. In this example, the period of the "stack sensitivity" variation $\Delta\lambda_s$ is 0.21 nm.

In order to optimize the radiation measured at the detector, it is necessary for the inspection apparatus to have a spectral resolution that is better than the size of the periodic variations of the stack sensitivity $\Delta\lambda_s$. Specifically, in order to fully resolve the periodic variations of the stack sensitivity, the required spectral resolution $\Delta\lambda_r$ of the inspection apparatus should be at least double that of the variation period $\Delta\lambda_s$. In the present example, therefore, the required spectral resolution $\Delta\lambda_r$ for the inspection apparatus may be approximately 0.1 nm.

It has been suggested to use the target structure (e.g., a grating structure) being measured to spectrally resolve the measurement radiation onto a camera or similar device. The spectral resolution of such an inspection apparatus will then be determined by the properties of the optical system and the properties of the target structure. Due to target size constraints, the spot diameter of a typical inspection apparatus is limited to approximately 2 μm. Assuming that the illuminating radiation is a Gaussian beam, the following relation between the beam waist diameter D and the numerical aperture of the illuminating radiation NA can be derived:

$$D = \frac{2}{\pi} \frac{\lambda}{NA} \quad (2)$$

For illuminating radiation with a wavelength of $\lambda$=13 nm, the numerical aperture can be derived as NA=4 mrad for the specific spot diameter mentioned above.

Presently, the pitch of product structures is approximately P=40 nm. The spectral resolution of a diffraction-based inspection apparatus (e.g. a scatterometer) measuring a target structure with this pitch can be derived as: $\Delta\lambda \approx 2P \times NA = 80 \times 0.004 = 0.32$ nm. The spectral resolution provided by the inspection apparatus is larger than the required 0.1 nm. This means that it is not possible to adequately resolve the periodic variations of the stack sensitivity in this way. It is possible to improve the spectral resolution of the inspection apparatus by reducing the size of the numerical aperture. However, this will in turn require the target size to be increased. This is because a decrease in NA will result in a larger spot diameter. Target structures should be preferably "underfilled" (i.e. the spot diameter is smaller than the size of the target). If the spot diameter is increased, the size of the target must therefore also be increased proportionally. Larger targets take up more space on the surface of a substrate, which is undesirable in a production environment since it, for example, increases the per-product manufacturing costs.

By way of specific metrology example, soft X-ray DBO (Diffraction-Based Overlay metrology) may make use of near normal incidence illumination, which enables the measurement radiation to penetrate the stack (structure or target being measured) deeply. This may cause ringing effects for thick stacks (e.g., relative to the measurement radiation wavelength). Without sufficient spectral resolution, these ringing effects will average out the DBO sensitivity towards zero, which is unacceptable.

In another specific metrology example, for soft X-ray OCD (Optical Critical Dimension metrology) and ARO (At-Resolution Overlay metrology, i.e. reconstruction based overlay metrology, without the need for biased targets) a high spectral resolution is desirable to maximize the information content of the measured signal (i.e. to prevent averaging out of information). Also, a large spectral range may be desirable, so large that it may cause overlapping diffraction orders. If overlapping orders occur in a grating based reference branch, it will cause illumination intensity normalization (i.e., multiplicative noise suppression) to fail.

In the following, a method and apparatus that improves the spectral resolution of the inspection apparatus will be described.

An illumination source is described, such as a HHG source, which generates (e.g., high harmonic) measurement radiation from first pump radiation beam at a first wavelength (or centered on a first wavelength) and second pump radiation beam at a second wavelength (or centered on at least a second wavelength). The generated measurement radiation (e.g., corresponding harmonics of the measurement radiation) generated by the first and second pump radiation beams interfere causing a heterodyne signal or beat at a beat frequency dependent on said first and second wavelengths. The difference in the first and second wavelengths should be small, e.g. 1 nm or smaller. In an embodiment, the wavelength difference will be much smaller than this; for example the difference (expressed in terms of frequency) may be smaller than 100 MHz, smaller than 10 MHz, smaller than 1 MHz, smaller than 0.1 MHz, smaller than 10 kHz or smaller than 1 kHz. This signal may be measured over a specific time interval and analyzed, for example by performing a Fourier transform, to extract or reconstruct the spectral composition of this measured signal.

Figure 4:
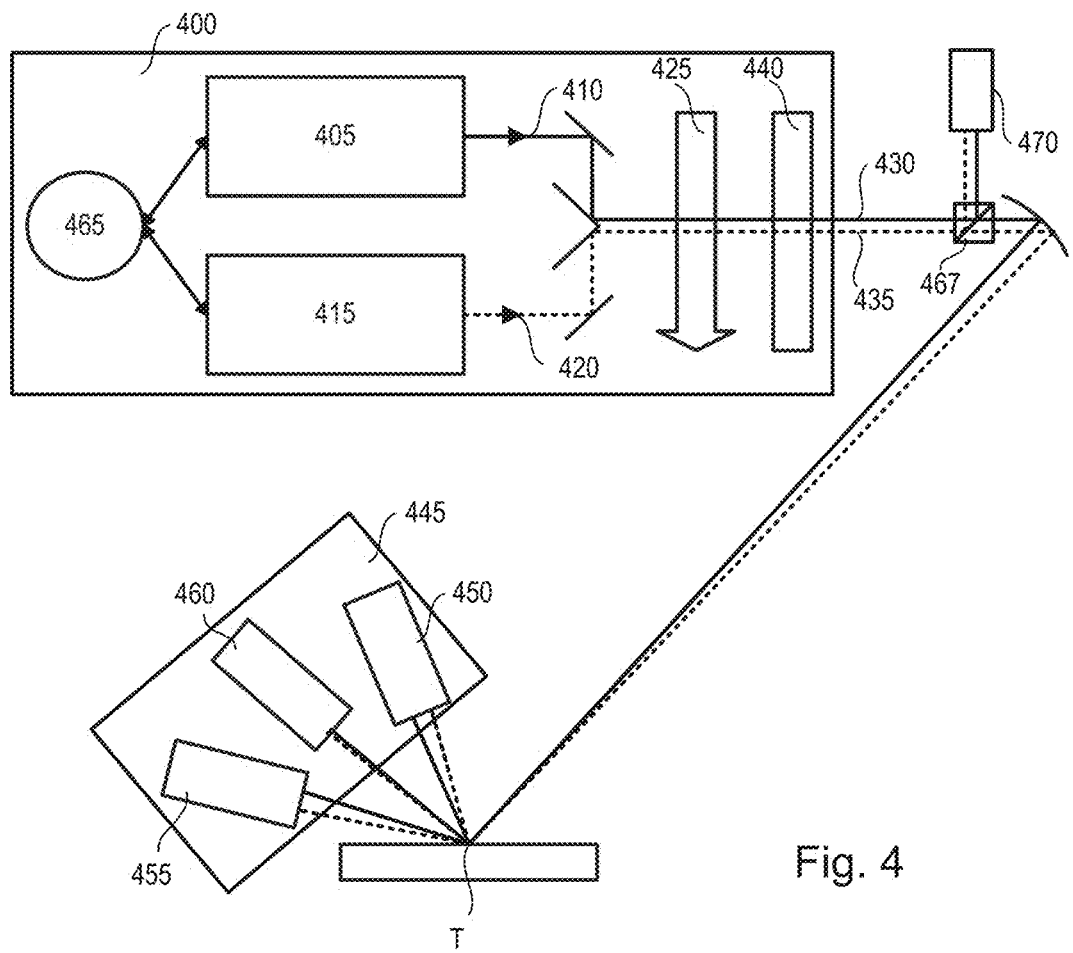
FIG. 4 is a schematic diagram of an inspection apparatus according to an embodiment of the invention.

FIG. 4 comprises an embodiment of an inspection apparatus comprising an illumination system, which in this example comprises a HHG source 400, shown in an operational configuration measuring a target T. The HHG source 400 comprises a first pump radiation source 405 which emits a first pump radiation beam 410 at a first wavelength $\lambda$, and a second pump radiation source 415 which emits a second pump radiation beam 420 at (at least) a second wavelength $\lambda+\Delta$, where $\Delta$ is a small wavelength offset, for example smaller than 1 nm (possibly much smaller as described above) relative to first wavelength $\lambda$. It should be noted that, depending on the exact modulation technique, one or more "side bands" might possibly occur. In such a case, the second pump radiation beam 420 might not be centered on one unique single wavelength $\lambda+\Delta$. Instead, for example, two wavelengths may be present: $\lambda+\Delta$ and $\lambda-\Delta$. This might be expected when using amplitude modulation for example.

The first pump radiation beam 410 and second pump radiation beam 420 excite a HHG medium, such as HHG gas jet 425, in such a way that corresponding harmonics of first measurement radiation 430 (generated by first pump radiation beam 410) and second measurement radiation 435 (generated by second pump radiation beam 420) interfere generating a beat component (heterodyne signal) in the combined measurement radiation for each corresponding (higher order) harmonic pair at the detector block 445. HHG medium may, for example, comprise a medium other than a gas, such as a high harmonic generating solid.

Once passing through filter element (infra-red block) 440, which blocks out unwanted radiation wavelengths, first and second measurement radiation 430, 435 is then used to measure target T (via intervening optics not shown). The radiation scattered by target T will then be detected by detector block 445, where it interferes generating the beat component. In an embodiment, the detector block 445 comprises a first detector 450 for positive diffraction orders, a second detector 455 for negative diffraction orders and a third detector 460 for the zeroth diffraction order. However, in other embodiments, the detector block 445 may comprise only one detector (e.g., one of detector 450, detector 455 or detector 460) or two detectors (e.g., any two of detectors 450, 455, 460). Note that the (e.g., higher) diffraction orders captured by the detector(s) should not be confused with the high harmonic orders of the HHG spectrum.

In the embodiment illustrated, there are two distinct pump radiation sources to generate the first and second pump radiation beams. In such an embodiment, to obtain the necessary beat component, it is proposed that the first and second pump radiation source 405, 415 are mode-locked 465 (e.g., synchronized in time) such that the first and second pump radiation beams have a wavelength or frequency which differs by a small constant offset as described.

In an alternative embodiment, the first and second pump radiation beams may be generated from a single pump radiation source such that the two harmonic sources generated will be locked in phase. In such an embodiment, the wavelength offset may be obtained using an electro-optical modulator in one of the pump radiation beams, before the HHG gas jet. Examples of electro-optical modulators comprise non-linear crystals and/or fluids. The applied modulation may comprise frequency modulation and/or phase modulation and/or amplitude modulation. Other alternative modulation strategies to obtain the wavelength offset between the first and second pump radiation beams may comprise varying the position one beam excites the HHG gas jet/medium relative to the other, and/or varying the relative time delay between activation the pump laser beams. Other alternatives may comprise manipulating the HHG gas jet/medium such that the high harmonics generated by one pump radiation beam has a greater wavelength shift than the other pump radiation beam; for example by changing local gas pressure (or surface property if the medium is a solid) at the different locations excited by each pump radiation beam.

As is known, a HHG source can be thought to operate in two distinct modes. In a first mode, the resultant HHG frequency spectrum comprises distinct spikes or peaks, one at each generated harmonic order, thereby approximating a frequency comb. In a second mode of operation, the high harmonic orders are each considerably broader such that they overlap forming a broadband spectrum. The difference between these two modes of operation is the width of the pump laser pulse. A shorter time duration of the pump laser pulse, which eventually contributes to high harmonic generation, will result in a spectral broadening of the individual high harmonic orders. At a certain point, the individual orders will start to overlap with each other in frequency/wavelength (the point at which this overlap starts to occur essentially defines the crossover point between these two modes of operation).

Figure 5:
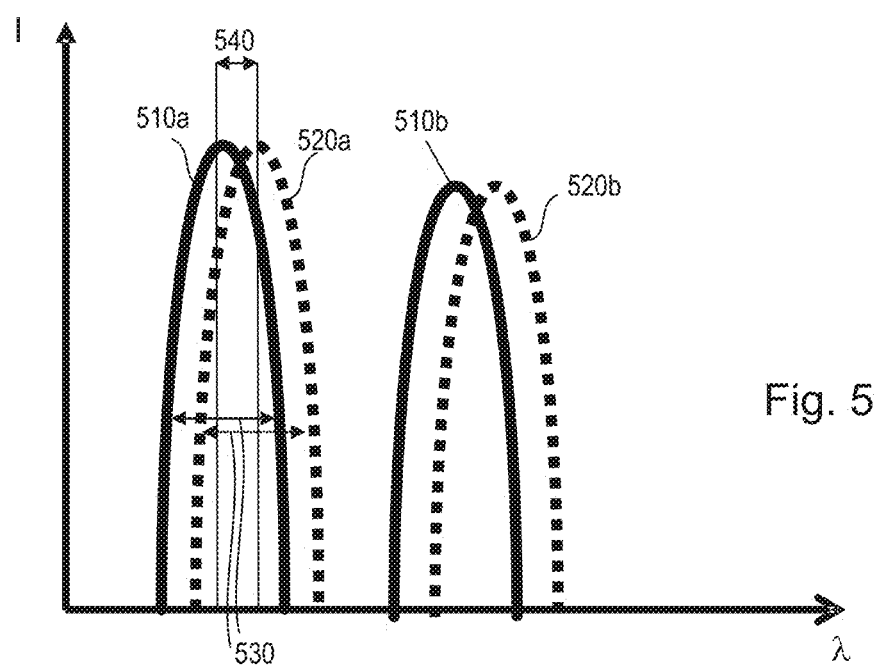
FIG. 5 is a plot of intensity I against wavelength λ of measurement radiation produced by the illumination source of the inspection apparatus of FIG. 4.

FIG. 5 is a plot of wavelength against intensity for the first mode of operation. Shown are two distinct higher orders 510a, 510b as generated by the first pump radiation beam and corresponding two distinct higher orders 520a, 520b as generated by the second pump radiation beam. For a first wavelength of 1030 nm for example, the 79th higher order 510a will result in a wavelength peak at approximately 13.0 nm. A typical bandwidth 530 of such an individual peak is 0.1 nm FWHM (Full Width Half Maximum). Note that only uneven higher-order harmonics are typically being generated in monatomic gasses (for reasons of symmetry). In an embodiment, the wavelength difference 540 between corresponding peaks is smaller than this bandwidth 530. Note that this wavelength difference 540 is dependent on the wavelength offset $\Delta\lambda$ of the pump radiation beams divided by m, where m is an integer which denotes the specific higher-order harmonic of the HHG source peak wavelength (e.g., m=79 for peaks 510a and 520a).

For each mth higher-order harmonic pair, a beat component will be present in the detected photo-current. The frequency of this beat component B will be m times that of the frequency difference between the two mode locked pump lasers; that is:

$$B = mc\left(\frac{1}{\lambda} - \frac{1}{(\lambda + \Delta)}\right) \quad (3)$$

where c is the speed of light.

Fourier Transform Spectroscopy techniques can be used to determine the spectral composition (e.g., intensity of each mth higher-order harmonic pair) from the variation of the detected signal over time, as modulated by the beat component. This may be done by means of a Fourier transform (integrated over the time variable). This may comprise computing the inner product of the detected signal with a sine or cosine shaped (single frequency) signal. Other transforms, such as Fourier-related transforms (e.g. cosine transform, Hartley transform, etc.) may also be used to spectrally resolve the signal.

Because the spectral information is not captured spatially, but rather temporally in the beat component of the measured signal, the individual detectors of the detector block (e.g. detector block 445) may be a simple photo-diode device rather than a camera (detector array). Such a photo-diode device may operate to capture the (diffracted) measurement radiation as a function of time, over a specific time period. Because the beat frequency of the beat component may be, for example, in the kHz range, the measurement radiation may be measured over a time period of the order of milliseconds (e.g., between 40 ms and 100 ms). Repeat samples of each of these measurements may be obtained to reduce noise.

Radiation sources used in metrology applications may suffer from illumination intensity and/or spectral fluctuations. To address this, conventional sources may use a separate reference branch to which measurement radiation is diverted by means of a beamsplitter or similar. Measurements using this reference branch can then be used to normalize any measurements. This reduces the number of photons available for actual measurement, and the requirement for the reference branch and beamsplitter adds cost and complexity. With the methods and apparatuses described herein, spectrally resolved individual zeroth diffraction order and/or higher diffraction order harmonics may be generated and separately measured. Therefore, more than one detector may be provided, for example, a detector for the zeroth diffraction order, as well as one or more detectors for one or more of the higher diffraction orders. In the specific example illustrated in FIG. 4, the detector block 445 comprises a first detector 450 for detecting one or more of the higher positive diffraction orders, a second detector 455 for detecting one or more of the higher negative diffraction orders and a third detector 460 for detecting the zeroth diffracted order. The detectors 450, 455, 460 should be located in the correct positions for capturing its corresponding diffraction order(s).

By doing this, the higher diffraction order measurement(s) can all be self-normalized with the corresponding zeroth diffraction order measurement, for example. This may be done, for example, by dividing a higher diffraction order measurement for a particular harmonic order m with the corresponding zeroth diffraction order measurement for that harmonic order m. It should be noted that any combination of corresponding diffraction orders can be used to achieve this self-normalization. Where the information regarding the parameter of interest is obtained from the zeroth diffraction order, one of the higher diffraction orders can be used to normalize the zeroth diffraction order. Or else, one higher diffraction order can be used to normalize another corresponding higher diffraction order. In this manner, the source illumination intensity fluctuations are eliminated from the detected measurements. Note that this form of self-normalization can also be applied to more traditional detection schemes, in which the dispersion of a grating in combination with an array detector is used to create spectral resolution. However, in an alternative embodiment, there may optionally be a beamsplitter 467 and reference detector 470 for providing a normalization signal.

Figure 6:
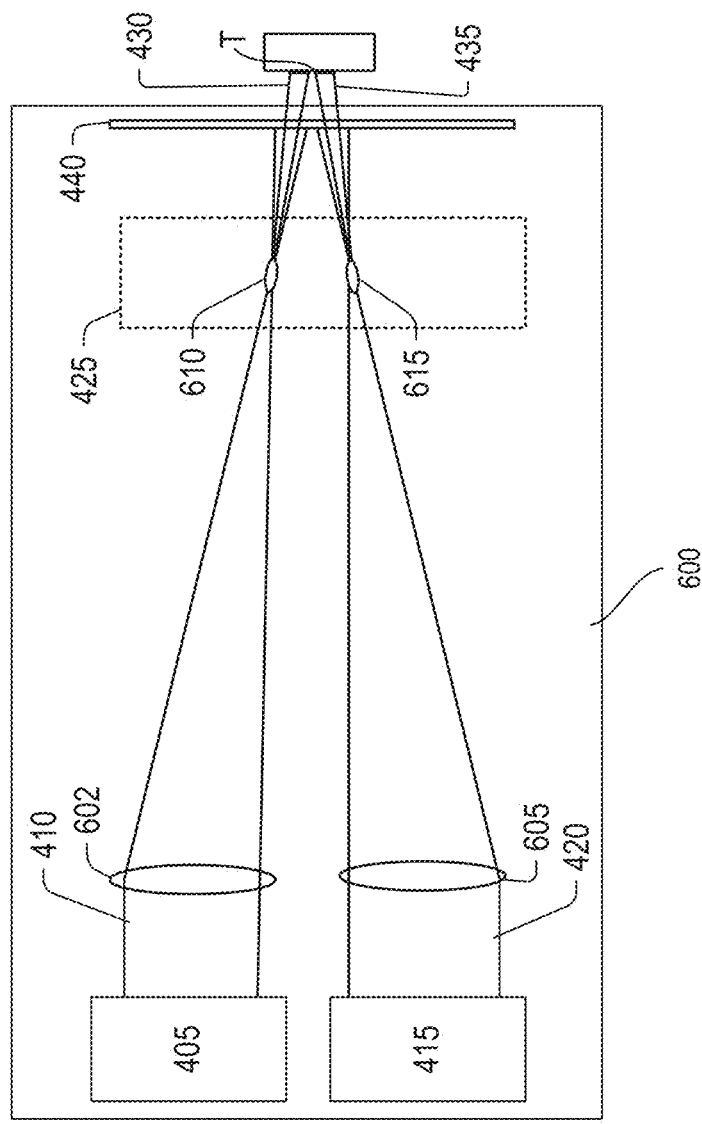
FIG. 6 is a more detailed schematic diagram the illumination source of the inspection apparatus of FIG. 4 according to an embodiment of the invention.

In order to obtain the desired beat component, the first and second pump radiation beams should be sufficiently close (spatially or temporally) to obtain the necessary interference. FIG. 6 illustrates a method for achieving this in a first embodiment. In the first embodiment, the beams are separated spatially, such that the first pump radiation beam and second pump radiation beam are each focused at two distinct locations within the HHG medium/gas. In such an embodiment, the first pump radiation beam and second pump radiation beam are not separated temporally, that is they are fired (activated) substantially (or approximately) simultaneously. The two distinct locations need to be sufficiently near to each other to result in interference, e.g., with a separation of between 10 μm and 100 μm. In this embodiment, the resulting two measurement radiation beams are imaged onto the target, resulting in two adjacent spots. The resulting electric field will interfere on the (e.g., photo diode) detector.

FIG. 6 shows an illumination system (HHG source) 600 which may, for example, be used in place of illumination system 400 shown in FIG. 4. A first pump radiation source 405 emits first pump radiation beam 410 with (or centered on) a particular wavelength $\lambda$ and second pump radiation source 415 emits second pump radiation beam 420 with (or centered on) at least one particular wavelength $\lambda+\Delta$. The first pump radiation beam 410 propagates to a first optical element 602 where it is focused at a first location 610 within HHG gas jet 425. Similarly, second pump radiation beam 420 propagates to a first optical element 605 where it is focused at a second location 615 within HHG gas jet 425. The locations 605 and 615 are sufficiently close such that the first pump radiation beam 410 and second pump radiation beam 420 interfere, as already described.

The first pump radiation beam 410 and the second pump radiation beam 420 interact with the gas to provide first measurement radiation 430 and second measurement radiation 435. This measurement radiation 430, 435 passes through an optical element 440 that suppresses unwanted radiation wavelengths (e.g., an IR filter). The first measurement radiation 430 and second measurement radiation 435 subsequently illuminates a target T at different locations (although the locations may alternatively overlap or partially overlap), resulting in interference of the diffracted measurement radiation, and therefore a measurable beat component, at the detector (not shown).

In an alternative embodiment, the first and second pump radiation beams are separated temporally, not spatially (i.e., they are focused at the same location in the HHG gas jet, or at least close enough that they overlap spatially, but are not fired simultaneously). Both pump radiation beams need to be 'fired' into the HHG gas with a sufficiently small time duration between them, so that they interfere. However, it may be that the gas atoms in the HHG gas jet might not have returned to their 'initial state' between each firing. In such an embodiment, the delay between firing the first and second pump radiation beams may be less than 20 fs, for example.

While the above description has been discussed in terms of a HHG source operating in a first "frequency comb" mode of operation, it should be appreciated that the difference between this first mode and the second described mode of operation is the difference is only a spectral broadening. This makes no essential difference for the heterodyne Fourier transform spectrometry methods described herein, and the concepts described are equally applicable to both of these first and second modes of operation.

Figure 7:
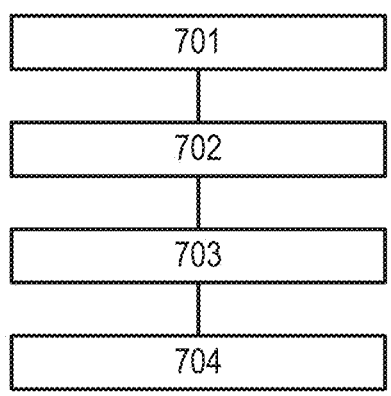
FIG. 7 is a flowchart describing a metrology method according to an embodiment of the invention.

FIG. 7 is a flowchart of a method of measuring a target or other structure on a substrate. The exemplary method may be implemented in an inspection apparatus such as the one shown in FIG. 3 or 4. As previously described, in a typical scatterometer based inspection apparatus the zeroth and/or higher (e.g. +1 and/or −1) diffraction orders of the radiation are used to determine a relevant property of the target structure (such as overlay or critical dimension).

In a first step 701, first measurement radiation and second measurement radiation are provided by an illumination system, such as HHG source 400, 600. As already described, as a consequence of a wavelength offset between the first and second pump radiation beams which respectively generate the first and second measurement radiation, corresponding harmonics generated by the first and second pump radiation beams interfere causing a heterodyne signal or beat at a beat frequency dependent on said first and second wavelengths.

In a second step 702, a target structure T is illuminated by the first and second measurement radiation. The combined measurement radiation is diffracted by the target structure into a number of diffraction orders, each of which is modulated by the beat component. The higher diffraction order and/or zeroth diffraction order radiation comprises the information from which a parameter of interest of the target structure will be determined. The zeroth diffraction order radiation comprises the portion of the combined illuminating radiation that is not diffracted by the target structure, but is reflected by the target structure.

In a third step 703, the reflected radiation beam is detected at a detector block, such as detector block 445. The third step may comprise detecting the scattered radiation (modulated with the beat component) as a signal (intensity) variation against time for one, some or each diffraction order. In an embodiment the higher positive diffraction orders are captured on a first detector (e.g., a photodiode), the negative diffraction orders are captured on a second detector and the zeroth diffraction order is are captured on a third detector.

In a fourth step 704, the detected radiation may be sent to a processing unit for further processing. In particular, the detected scattered radiation may be spectrally resolved using Fourier transformation to derive spectrally resolved measurement data. This step may also comprise self-normalizing one detected diffraction order with another detected diffraction order, for example one or more of the higher diffraction orders with the zeroth order. This self-normalizing step may be performed on the spectrally resolved data, per harmonic order. The processing step then determines one or more parameters of interest from the spectrally resolved measurement data using, for example, reconstruction or asymmetry determination techniques.

While the above description describes the illumination source in terms of a HHG source, the teachings described herein are not so limited, and other illumination sources which use a pump or seed radiation source to illuminate a gas medium fall within the scope of this disclosure.

Advantages of the illumination source and accompanying apparatuses and methods disclosed herein include:

Creation of high spectral resolution in combination with fast acquisition time.

There is no requirement for moving opto-mechanical parts. Other illumination sources may use moving one or more opto-mechanical devices to, for example, alter a path length of one measurement beam relative to another.

There is no requirement for a separate reference branch to correct for illumination intensity fluctuations.

There is no requirement for a separate optical element (in the region of the target) to measure the zeroth diffraction order spectroscopically Allows a large spectral range (i.e. wavelength range), thereby increasing the information content that is being measured and also the amount of photons being measured (to suppress photon shot noise).

No need to for a camera to detect the diffracted radiation, photo diodes can be used instead, which may reduce read noise, and possibly also cost and complexity.

More embodiments are disclosed in the subsequent numbered clauses:

1. An illumination source for generating measurement radiation for an inspection apparatus, operable to generate at least first measurement radiation and second measurement radiation such that said first measurement radiation and said second measurement radiation interfere to form combined measurement radiation modulated with a beat component.

2. An illumination source as claimed in claim 1, wherein said first measurement radiation and said second measurement radiation are spectrally coherent.

3. An illumination source as claimed in claim 1 or 2, wherein the first measurement radiation is centered on a first wavelength and the second measurement radiation comprises at least one component centered on a second wavelength.

4. An illumination source as claimed in claim 3, wherein the difference between said first wavelength and said second wavelength is smaller than 0.01 nm.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used in relation to the lithographic apparatus encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. An illumination source for generating measurement radiation for an inspection apparatus, configured to generate at least first measurement radiation and second measurement radiation such that said first measurement radiation and said second measurement radiation interfere to form combined measurement radiation modulated with a beat component, wherein said illumination source is a high harmonic generation source, and wherein the first measurement radiation is centered on a first wavelength and the second measurement radiation comprises at least one component centered on a second wavelength, the second wavelength being different than the first wavelength.

2. The illumination source of claim 1, wherein said first measurement radiation and said second measurement radiation are spectrally coherent.

3. The illumination source of claim 1, wherein the difference between said first wavelength and said second wavelength is smaller than 0.01 nm.

4. The illumination source of claim 1, wherein the frequency difference between the frequency of the first measurement radiation and the frequency of the second measurement radiation is less than 10 MHz, less than 100 kHz, or less than 1 kHz.

5. The illumination source of claim 1, wherein each high harmonic of the first measurement radiation and a corresponding harmonic of the second measurement radiation interfere to form said combined measurement radiation modulated with a beat component.

6. The illumination source of claim 5, wherein a wavelength difference of each high harmonic of the first measurement radiation and the corresponding harmonic of the second measurement radiation is smaller than the bandwidth of each of said corresponding high harmonics.

7. The illumination source of claim 5, comprising:
at least one pump radiation source configured to generate a first pump radiation beam centered on a first pump wavelength and a second pump radiation beam comprising at least one component centered on a second pump wavelength; and
a high harmonic generating medium;
wherein said at least one pump radiation source is arranged such that said first pump radiation beam excites said high harmonic generating medium to generate said first measurement radiation and said second pump radiation beam excites said high harmonic generating medium to generate said second measurement radiation.

8. The illumination source of claim 7, wherein said at least one pump radiation source comprises a first pump radiation source configured to generate said first pump radiation beam and a second pump radiation source configured to generate said second pump radiation beam; said first pump radiation source and said second pump radiation source being mode-locked or being phase-locked.

9. The illumination source of claim 7, wherein said at least one pump radiation source comprises a single pump radiation source; and
said illumination source comprises:
a beam splitting element to form said first pump radiation beam and said second pump radiation beam each centered on said first pump wavelength; and
a modulator device configured to modulate said second pump radiation beam, centering it on at least said second pump wavelength.

10. The illumination source of claim 7, wherein said first pump radiation beam and said second pump radiation beam are configured to excite different locations within said high harmonic generating medium at substantially the same time.

11. The illumination source of claim 7, wherein said first pump radiation beam and said second pump radiation beam are configured to excite the substantially same location within said high harmonic generating medium at different times.

12. An illumination source for generating high harmonic radiation configured to generate at least first high harmonic radiation and second high harmonic radiation, such that said first high harmonic radiation and said second high harmonic radiation interfere to form combined high harmonic radiation modulated with a beat component.

13. The illumination source of claim 12, wherein said first high harmonic radiation and said second high harmonic radiation are spectrally coherent.

14. The illumination source of claim 12, wherein the first high harmonic radiation is centered on a first wavelength and the second high harmonic radiation comprises at least one component centered on a second wavelength.

15. The illumination source of claim 14, wherein the difference between said first wavelength and said second wavelength is smaller than 0.01 nm.

16. The inspection apparatus, comprising:
- an illumination source configured to generate at least first measurement radiation and second measurement radiation such that said first measurement radiation and said second measurement radiation interfere to form combined measurement radiation modulated with a beat component, wherein said illumination source is a high harmonic generation source, and wherein the first measurement radiation is centered on a first wavelength and the second measurement radiation comprises at least one component centered on a second wavelength, the second wavelength being different than the first wavelength;
- an illumination system configured to illuminate a target structure with the measurement radiation resulting in scattered radiation modulated with the beat component;
- a detector configured to detect the scattered radiation; and
- a processor configured to use said beat component to spectrally resolve said scattered radiation.

17. A method of measuring a target structure on a substrate comprising:
- generating at least a first measurement radiation and a second measurement radiation such that said first measurement radiation and said second measurement radiation interfere to form combined measurement radiation modulated with a beat component in a high harmonic generation source; and wherein the first measurement radiation is centered on a first wavelength and the second measurement radiation comprises at least one component centered on a second wavelength, the second wavelength being different than the first wavelength;
- illuminating the target structure with the measurement radiation resulting in scattered radiation modulated with the beat component;
- detecting the scattered radiation; and
- processing the detected scattered radiation, said processing comprising using said beat component to spectrally resolve said scattered radiation.

18. A non-transitory computer readable medium comprising machine readable instructions which, when run on a suitable processor, cause the processor to perform a method for measuring a target structure on a substrate comprising:
- generating at least a first measurement radiation and a second measurement radiation such that said first measurement radiation and said second measurement radiation interfere to form combined measurement radiation modulated with a beat component in a high harmonic generation source, and wherein the first measurement radiation is centered on a first wavelength and the second measurement radiation comprises at least one component centered on a second wavelength, the second wavelength being different than the first wavelength;
- illuminating the target structure with the measurement radiation resulting in scattered radiation modulated with the beat component;
- detecting the scattered radiation; and
- processing the detected scattered radiation, said processing comprising using said beat component to spectrally resolve said scattered radiation.

19. An illumination source for generating measurement radiation for an inspection apparatus comprising:
- at least one pump radiation source configured to generate a first pump radiation beam centered on a first wavelength and a second pump radiation beam centered on a second wavelength; and
- a high harmonic generating medium;
- wherein said at least one pump radiation source is arranged such that said first pump radiation beam excites said high harmonic generating medium to generate first measurement radiation and said second pump radiation beam excites said high harmonic generating medium to generate second measurement radiation, and such that said first measurement radiation and said second measurement radiation interfere to form combined measurement radiation modulated with a beat component.

* * * * *